United States Patent [19]

Hoffman

[11] Patent Number: 5,450,293
[45] Date of Patent: Sep. 12, 1995

[54] FINGER MOUNTED FIBER OPTIC ILLUMINATION SYSTEM

[76] Inventor: Elliott S. Hoffman, 5001 Desert Jewel Dr., Paradise Valley, Ariz. 85253

[21] Appl. No.: 175,798

[22] Filed: Dec. 30, 1993

[51] Int. Cl.6 ............................ F21V 8/00; F21L 15/08
[52] U.S. Cl. ............................ 362/32; 362/103; 362/804; 600/182
[58] Field of Search ............ 362/32, 103, 109, 119, 362/183, 804; 128/23; 433/29, 30, 31

[56] References Cited

U.S. PATENT DOCUMENTS

| | | |
|---|---|---|
| 1,245,817 | 11/1917 | Suserud . |
| 1,745,570 | 2/1929 | Pickett . |
| 3,397,457 | 8/1968 | Gosselin . |
| 3,504,984 | 4/1970 | Bush ............................ 356/256 |
| 3,590,232 | 6/1971 | Sodowski ........................ 240/2 |
| 3,592,199 | 7/1971 | Ostensen ......................... 128/23 |
| 3,614,414 | 10/1971 | Gores .............................. 362/32 |
| 3,809,072 | 5/1974 | Ersek et al. .................... 128/23 |
| 4,616,257 | 10/1986 | Kloots et al. .................. 358/93 |
| 4,770,486 | 9/1988 | Wang et al. ..................... 362/32 |
| 4,991,069 | 2/1991 | Tiller ............................ 362/109 |
| 5,003,434 | 3/1991 | Gonser et al. .................. 362/32 |
| 5,086,378 | 2/1992 | Prince ........................... 362/103 |
| 5,115,382 | 5/1992 | Smith ............................ 362/183 |

Primary Examiner—Stephen F. Husar
Assistant Examiner—Y. Quach
Attorney, Agent, or Firm—Cahill, Sutton & Thomas

[57] ABSTRACT

A fiber optic illumination system is supported upon the wrist and finger of a dentist, oral surgeon, or physician for lighting the oral cavity or other field of operation. A wrist-supported case houses a light bulb, battery, and switch for providing a source of light. A flexible fiber optic conductor conveys the light from the wrist-supported case to a finger supported lens for directing the beam of light in a direction controlled by movements of the finger. A quick release coupling allows the fiber optic conductor to be removed from the wrist supported case for sterilization of the components that come in contact with the patient. A remote light source can also be coupled to a light tunnel within the wrist-supported case for supplying light to the finger-supported lens.

1 Claim, 3 Drawing Sheets

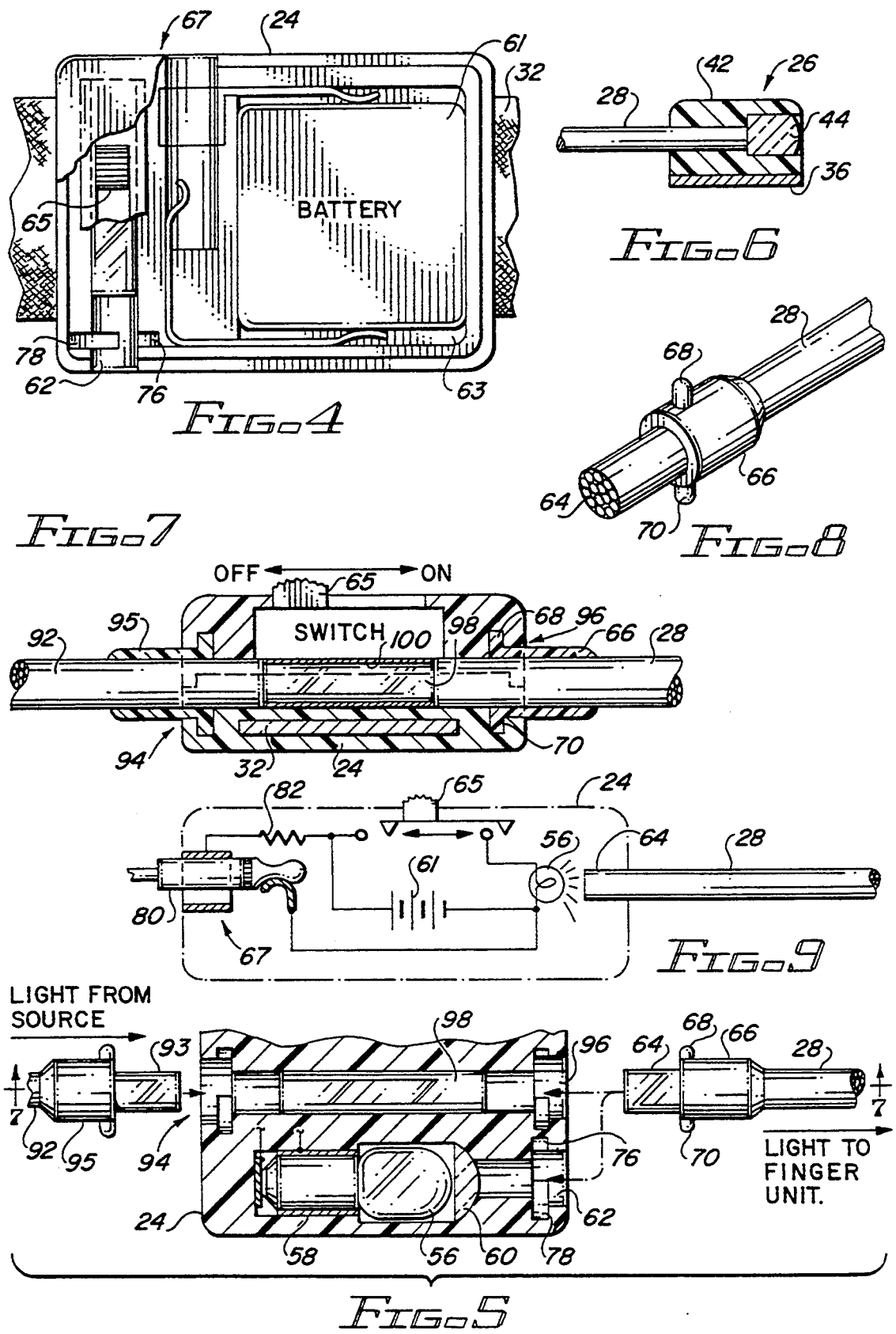

FINGER MOUNTED FIBER OPTIC ILLUMINATION SYSTEM

BACKGROUND OF THE INVENTION

1. Field of the Invention

The present invention relates generally to apparatus for illuminating a field of operation within the intra-oral cavity of a patient's mouth, and more particularly, to a finger mounted fiber optic illumination system for use by dentists, oral surgeons, and the like.

2. Description of the Relevant Art

Dentists, oral surgeons, and other physicians who operate within a patient's mouth require adequate illumination of the field of operation in order to work most effectively. Numerous methods have been used in the past in an attempt to provide adequate illumination of the field of operation.

First, overhead lights equipped with parabolic mirrors and polarizing lenses have been used as a general source of non-glare lighting within dental examination offices and within operating rooms. However, such overhead lights must often be redirected during dental or medical procedures to keep the light directed at the point of interest, and the need to readjust the overhead light creates a distraction and requires additional time. Moreover, when the dentist, oral surgeon, or physician must lean over the patient to closely observe the field of operation, the overhead light is blocked. In addition, the light source is so far removed from the patient that it is often not possible to direct the overhead light source deep within the patient's oral cavity.

It is also known to support a light source from a headband worn by a physician to illuminate an area being viewed by the physician. For example, within U.S. Pat. No. 4,616,257 to Kloots et al., a medical headlight apparatus is disclosed wherein a fiber optic cable transmits light to a headband worn by the physician. The headband supports a housing including an illuminating lens for directing light transmitted by the fiber optic cable toward the field being viewed by the physician. While being an improvement over the above-described overhead light source, the medical headlight apparatus disclosed by Kloots et al. still does not permit the physician or other user to position the light source closely proximate the patient's mouth or other field of operation, and accordingly, the user's hands may block the light from reaching the desired region within the field of operation.

Moreover, many dentists and oral surgeons are now being required to wear facial splash guards during oral dental and medical procedures. These splashguards are typically supported about the head of the user. As a practical matter, it is a nuisance to wear both a facial splash guard and a headband mounted light source during such procedures.

Within the dental field, it is also known to incorporate a fiber optic light conductor within a dental handpiece for directing a beam of light at the area of the mouth at which the end of the dental handpiece is being directed. For example, U.S. Pat. No. 3,397,457 to Gosselin, U.S. Pat. No. 3,590,232 to Sadowski, and U.S. Pat. No. 5,003,434 to Gonser et al. all relate to dental hand-tools provided with fiber optic illumination sources that are either attached to, or incorporated within, a dental handpiece for illuminating the area of the patient's mouth at which such dental instruments are directed. While such apparatus helps to illuminate the patient's mouth during drilling operations, the light source is part of the dental handpiece and is not available unless the dentist keeps the dental handpiece within the patient's mouth.

Dental handpieces are commercially available wherein the fiber optic cable that provides the source of light is bundled together with the pressurized air hose and exhaust hose used to operate the high speed turbine drill head within such dental handpiece. Such dental handpieces also may include yet another hose for conducting water to the tip of the dental handpiece for cooling the drill and/or the area of the patient's mouth that is being drilled. All of these hoses must be passed through the dental handpiece, and accordingly, their are limitations imposed upon the size of the fiber optic cable that can be passed into the dental handpiece for purposes of illumination. Limitations placed upon the size/diameter of the fiber optic cable necessarily limit the amount of light that can be directed into the patient's mouth.

In addition, dental handpieces that include fiber optic light paths and light emitting lenses tend to be significantly more expensive than those dental handpieces which omit such fiber optic light paths. While the cost of a single dental handpiece incorporating fiber optic lighting could be borne by most dentists, such dental handpieces must be sterilized in an autoclave between uses in order to prevent the transmission of infectious diseases from patient to patient. The requirement for sterilization between uses effectively requires a dentist to maintain several of such dental handpieces in a dental office to avoid delays between patient examinations. Thus, the additional cost of a dental handpiece equipped with a fiber optic lighting channel is multiplied several times.

Accordingly, it is an object of the present invention to provide a fiber optic illumination system for dentists, oral surgeons, physicians and the like, for illuminating the oral cavity or other field of operation, wherein the light source can be positioned closely proximate the oral cavity or other field of operation.

It is another object of the present invention to provide such an illumination system wherein the light source can easily be directed by the user at a selected location within the oral cavity or other field of operation.

It is still another object of the present invention to provide such an illumination system that is compact to avoid restrictions upon the mobility of the user and to avoid interference with other dental or medical tools that must be inserted into the field of operation.

A further object of the present invention is to provide such an illumination system which can be supported independently from a dental handpiece or other tool.

A yet further object of the present invention is to provide such an illumination system wherein the size and diameter of the fiber optic path are not restricted by the dimensions of a dental handpiece.

Another object of the present invention is to provide such an illumination system which can be sterilized between uses easily and economically.

Still another object of the present invention is to provide such an illumination system which is inexpensive to construct and which is easy to use.

Yet another object of the present invention is to provide such an illumination system which can be used with fiber optic light sources that may already be present within the dental or medical office.

These and other objects of the present invention will become more apparent to those skilled in the art as the description of the present invention proceeds.

SUMMARY OF THE INVENTION

Briefly described, the present invention provides a dental lighting device for allowing a dentist, oral surgeon, physician, or the like (hereinafter collectively referred to as "dentist") to selectively illuminate a portion of a patient's mouth, and including a case and a mechanism for releasably supporting the case upon the dentist's arm; preferably, this mechanism takes the form of a wrist strap for supporting the case upon the dentist's wrist.

In a first form of the present invention, a light source is supported by the case for providing the light used to illuminate the patient's mouth. In a second form of the present invention, the source of light is remotely located and coupled to the case. In both forms of the present invention, a fiber optic light conductor having first and second opposing ends is provided for conducting light from the case to an area proximate one of the dentist's fingers.

The present invention also includes a coupling mechanism for detachably coupling the first end of the fiber optic light conductor to the case for causing light to be conducted through the fiber optic light conductor toward the second end thereof for being emitted from the second end of the fiber optic light conductor proximate one of the dentist's fingers. A finger support mechanism, for example, a ring or band, is provided for supporting the second end of the fiber optic light conductor upon the dentist's finger for directing light emitted from the second end of the fiber optic light conductor into the patient's mouth.

The above-described coupling mechanism that is used to detachably couple the first end of the fiber optic light conductor to the case allows the fiber optic light conductor and its finger support mechanism to be detached from the case for allowing the fiber optic light conductor and finger support mechanism to be sterilized between uses in a sterilization apparatus independently of the remaining components (light source, case, wrist band). Accordingly, assuming that a plurality of such fiber optic light conductors and related finger support mechanisms are provided, the dentist need not wait for the first such fiber optic light conductor and related finger support mechanism to be sterilized before moving on to a second patient.

In the first form of the present invention, the light source includes a light bulb disposed within the case itself for emitting light. One or more electrical batteries are disposed within the case for providing electrical power to the light bulb, and an electrical switch extends from the case for operation by the dentist to selectively couple the batteries to the light bulb when illumination is required. The batteries are preferably of the rechargeable type, and the case includes an electrical jack adapted to receive an electrical power plug from an external battery charger to periodically recharge the batteries, for example, at the end of each day.

As mentioned above, an important feature of the present invention is the detachable coupling between the case and the first end of the fiber optic light conductor. This detachable coupling mechanism preferably includes an output light jack supported by the case proximate the light source. This output light jack includes an opening for releasably receiving the first end of the fiber optic light conductor. In one preferred form, the opening of the output light jack is cylindrical and has an internal diameter commensurate with the diameter of the first cylindrical end of the fiber optic light conductor in order to form a friction fit therebetween. In a second preferred embodiment, a more positive, yet detachable, coupling is formed between the case and the first end of the fiber optic light conductor by securing a first connector proximate the first end of the fiber optic light conductor, and providing a second mating connector at the output light jack for releasably and rotatably engaging the first connector for releasably retaining the first end of the fiber optic light conductor within the opening of the jack. Examples of such mating connectors include bayonet-style connectors and threaded luer lock connectors.

In the second form of the present invention, the light source is located remotely from the case worn about the dentist's wrist. A separate fiber optic light conductor is used to convey light from the light source into the wrist-mounted case. A first end of this separate fiber optic light conductor is coupled to the remote light source for causing light to be conducted therethrough for emission by the second end thereof. The second end of this separate fiber optic light conductor is coupled to the case for introducing light thereto; the aforementioned coupling between the second end of the separate fiber optic light conductor and the case is preferably a detachable coupling for allowing the case to be disconnected therefrom when desired. The case includes a light coupling path, such as a light transit tunnel, for directing light emitted by the second end of the separate fiber optic light conductor into the first end of the fiber optic light conductor that is detachably coupled to the output light jack.

BRIEF DESCRIPTION OF THE DRAWINGS

FIG. 4 is a sectional view of the wrist-supported component shown in FIG. 3 taken through the plane designated by lines 4—4 in FIG. 3.

FIG. 5 is a partial sectional view of the wrist-supported component of the illumination system and illustrating both a locally-generated light source as well as a light tunnel for conveying light supplied by a remote light source.

FIG. 6 is a sectional view through the finger-supported component of the illumination system taken through the plane designated by lines 6—6 within FIG. 3.

FIG. 7 is a sectional view of the wrist-supported component of the illumination system taken through the plane designated by lines 7—7 within FIG. 5 and illustrating both a power switch and the aforementioned light tunnel.

FIG. 8 is a perspective view of a fiber optic light cable equipped with a quick-release bayonet-style end connector for allowing the fiber optic light cable to be releasably coupled to the wrist-supported component of the illumination system.

FIG. 9 is a schematic drawing illustrating the light bulb, rechargeable batteries, power switch, and battery recharging circuit included within the wrist-supported component of the illumination system.

DETAILED DESCRIPTION OF THE PREFERRED EMBODIMENTS

Figure 1:
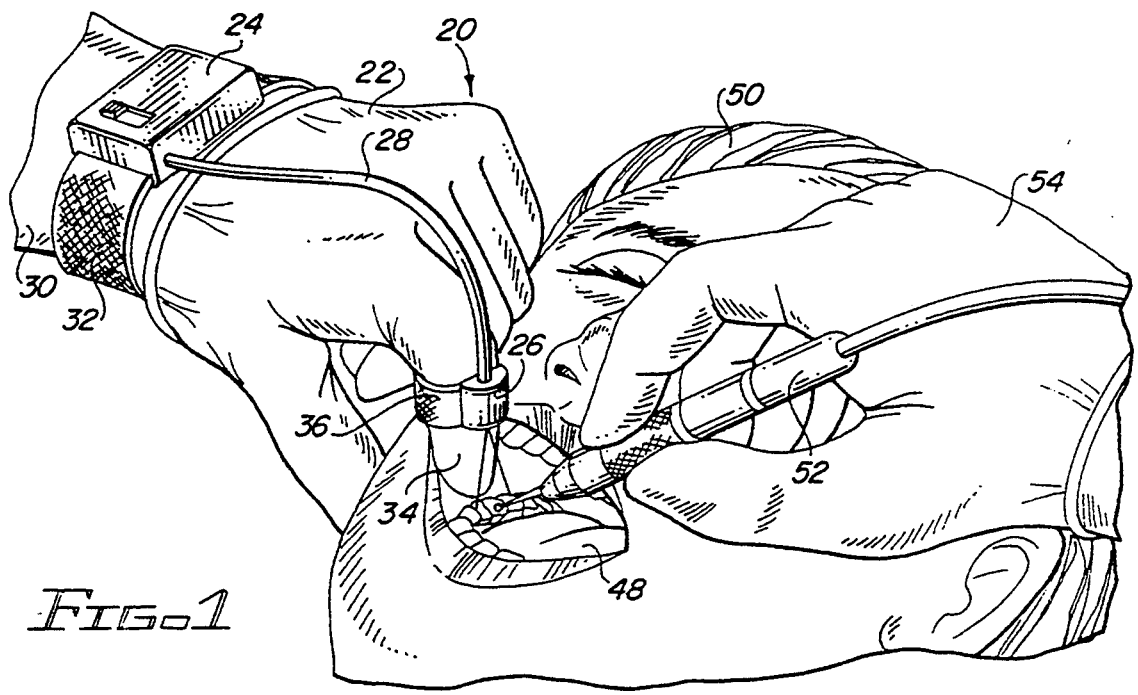
FIG. 1 is a perspective view showing a finger mounted fiber optic illumination system constructed in accordance with a preferred embodiment of the present invention in use by a dentist during a dental drilling procedure.
Figure 2:
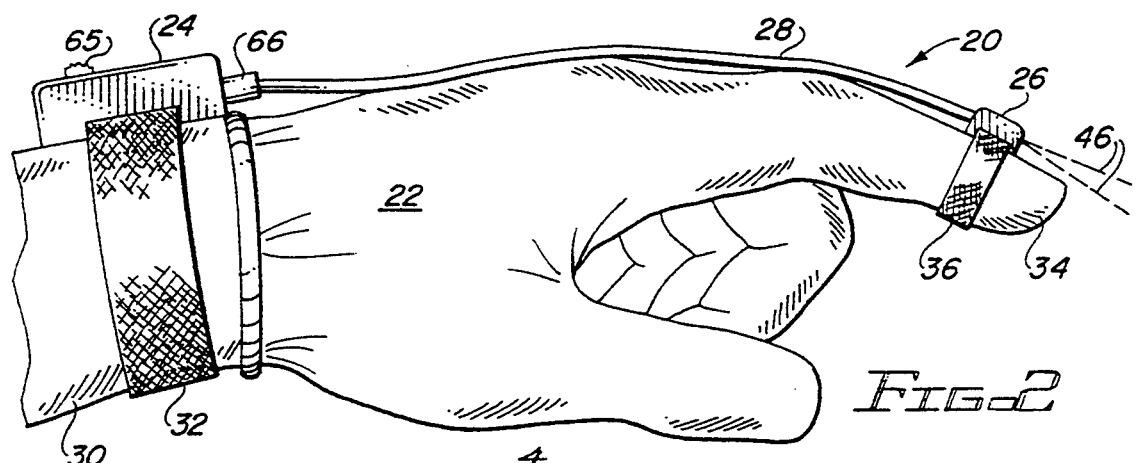
FIG. 2 is a side view of the fiber optic illumination system shown in FIG. 1.
Figure 3:
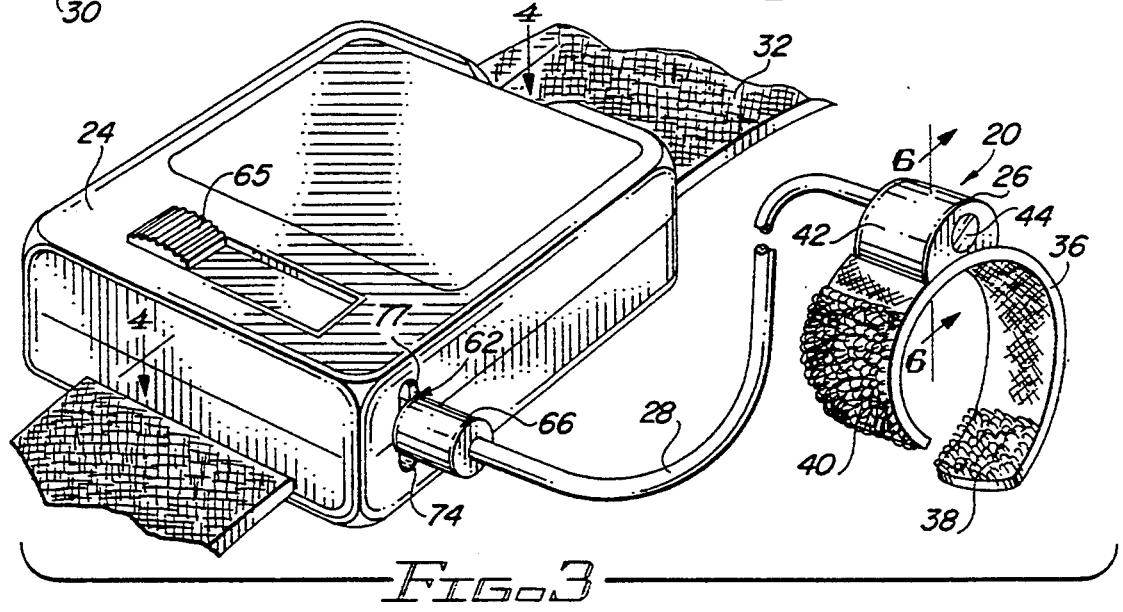
FIG. 3 is a perspective view of the two principle components of the fiber optic illumination system shown in FIGS. 1 and 2.

A dental lighting device which includes a finger mounted fiber optic illumination system that forms a preferred embodiment of the present invention is shown in FIGS. 1–3. Within FIGS. 1–3, the lighting device is designated generally by reference numeral 20. Within FIGS. 1 and, lighting device 20 is shown being worn upon the left hand 22 of a dentist, although those skilled in the art will appreciate that lighting device 20 may be worn on either hand. As shown in FIGS. 1 and 2, lighting device 20 includes a wrist-supported component in the form of a case or housing 24, a finger-supported component 26, and a flexible fiber 4 optic light conductor 28 extending therebetween, with its first end coupled to case 24 and its second opposing end coupled to finger-supported component 26. In the preferred embodiment, fiber optic light conductor is of the type commercially available from Edmund Scientific and measures approximately ⅛ to 3/16 inches in diameter.

Still referring to FIGS. 1–3, case 24 is releasably supported about the dentist's wrist 30 by a wrist band or strap 32 that extends about the dentist's wrist 30. Likewise, finger-supported component 26 is releasably supported about the dentist's index finger 34 by a finger ring or band 36. As shown in FIG. 3, finger band 36 may take the form of a flexible strip having a first hooked VELCRO brand fabric segment 38 on the inside of one end of the band and a second mating looped VELCRO brand fabric segment 40 on the outside of the second end of the band. Such a flexible strip allows finger-supported component 26 to be quickly and easily secured about a dentist's finger, and to be quickly removed therefrom, while providing a convenient means for adjusting the diameter of the band to fit different sized fingers. While not shown, the ends of wrist band 32 may be similarly provided with mating portions of VELCRO brand hooked and looped fabric for releasably securing the ends of wrist band 32.

As shown in FIGS. 3 and 6, finger supported component 26 includes a crescent-shaped base 42 and a lens 44 for directing light conducted by fiber optic light conductor 28 and emitted from the second end thereof. The light beam emitted by lens 44 is illustrated by dashed lines 46 in FIG. 2. Referring again to FIG. 1, finger-supported component 26, including base 42 and lens 44, are supported near the first knuckle of index finger 34.

Accordingly, as the dentist inserts the tip of his or her index finger 34 into the patient's mouth to displace soft tissues within the oral cavity away from the field of operation, light beam 46 is positioned proximate the mouth 48 of the patient 50 for allowing the dentist to selectively illuminate a portion of the patient's mouth 48. By merely pointing the tip of index finger 34 forward, backward or to either side, the dentist can redirect the beam of light 46 to any desired point in the field of operation. Moreover, as shown in FIG. 1, light beam 46 can be positioned independently of dental handpiece 52 which is held in the dentist's other hand 54. In addition, because the length of fiber optic light conductor 28 extending between the user's wrist and finger is relatively short, and because it is fastened to the user's wrist and finger, the light conductor is not likely to become caught or tangled during use.

In a first embodiment of the present invention, a light source is housed within and supported by case 24 for providing a source of light that is conducted by fiber optic conductor 28 to lens 44. Referring to FIG. 5, light bulb 56 is supported within a socket 58 formed in case 24 for emitting light and is electrically interconnected with first and second electrical terminals of socket 58. Lens 60 is disposed in case 24 just ahead of light bulb 56 and focuses the light emitted by light bulb 56 into a light output port 62 of case 24. A battery 61 is supported within chamber 63 of case 24 for providing electrical power to light bulb 56. A slide switch 65 (see FIGS. 3, 4, and 7) selectively couples the battery 61 to the electrical terminals of socket 58 in order to conserve the battery when lighting device 20 is not in use. Battery 61 may be a non-rechargeable battery, if desired. However, in the preferred embodiment of the present invention, battery 61 is a rechargeable battery; as shown in FIG. 4, an electrical jack 67 may also be provided in case 24 for releasably receiving an electrical plug of an external electrical charging circuit (not shown) in order to receive electrical power to recharge the battery periodically, e.g., overnight.

Light output port 62 is in the form of a cylindrical bore or opening and has an internal diameter that is commensurate with the outer diameter of the cylindrical first end 64 of fiber optic light conductor 28. Thus, light output port 62 provides a jack into which the first end 64 of fiber optic light conductor 28 can be coupled for being positioned proximate light bulb 56. Light output port 62 detachably couples first end 64 of fiber optic light conductor 28 to case 24 for causing light provided by light bulb 56 to be conducted through fiber optic light conductor 28 toward the second end thereof for being emitted through lens 44. First end 64 of fiber optic light conductor 28 is releasably received within light output port 62 in a manner which allows fiber optic light conductor 28 to be quickly and easily attached to or removed from case 24.

The releasable connection between first end 64 of fiber optic light conductor 28 and light output port 62 of case 24 can simply be a friction fit connection, if desired, in order to releasably retain the first end of the fiber optic light conductor within light output port jack 62. However, in the preferred embodiment of the present invention, a quick-release bayonet-style connection is formed between first end 64 of fiber optic light conductor 28 and light output port 62 of case 24. A connector 66 is secured about fiber optic light conductor 28 proximate to, but recessed a short distance from, first end 64 thereof. Connector 66 is generally cylindrical but includes two projecting tabs 68 and 70 (see FIGS. 5 and 8) extending outwardly in opposing directions from the periphery thereof. As shown in FIG. 3, case 24 includes a pair of slotted openings 77 and 74 extending from light output port jack 62 for receiving tabs 68 and 70 of connector 66. Referring to FIG. 5, case 24 also has a pair of annular recesses 76 and 78 which are continuous with slotted openings 77 and 74 and which are adapted to receive and releasably interlock with tabs 68 and 70 of connector 66 when the first end of fiber optic light conductor 28 is inserted into light output port 62 and rotated through a ninety-degree angle. Thus, slotted openings 77 and 74 and annular recesses 76 and 78 together form a second connector that releasably and rotatably engages first connector 66 for releasably retaining the first end of fiber optic light conductor 28 within light output port 62.

The significance of the detachable coupling formed between first end 64 of fiber optic light conductor 28 and the light output port 62 of case 24 relates primarily to the ability of the user to conveniently and inexpensively sterilize those portions of lighting device 20 which come in contact with the patient. Such sterilization procedures typically require that the components to be sterilized be placed in an autoclave and raised to a temperature of approximately 250 degrees Fahrenheit for a period of 30 minutes to ensure that such components are sterile. Fiber optic light conductor 28 and finger-supported component 26 (including finger band 36, base 42, and lens 44) are made of materials which can withstand the temperature of the autoclave without harm. In contrast, the components housed within case 24 may not be able to withstand the temperatures and pressures of an autoclave during sterilization procedures. Therefore, the ability to quickly detach first end 64 of fiber optic light conductor 28 from case 24 facilitates sterilization of fiber optic light conductor 28 and finger-supported component 26 between uses while avoiding the need to insert case 24 within the sterilization apparatus and thereby subjecting case 24 and its components to extreme temperatures or pressures.

Moreover, fiber optic light conductor 28 and finger-supported component 26 can be constructed inexpensively, for allowing a dentist, oral surgeon, or other physician to purchase a relatively large number of such components, all for use with a single case 24. This permits the dentist or other user to attach a first sterilized fiber optic light conductor 28 and finger-supported component 26 to his or her wrist-supported case 24 before treating a first patient, to remove the first assembly from case 24 after treating the first patient, and to quickly attach a second sterilized fiber optic light conductor 28 and finger-supported component 26 to his or her wrist-supported case 24 before treating a second patient, without waiting for the first assembly to be sterilized, and without removing wrist-supported case 24. In addition, since the dentist or other user can purchase only a single wrist-supported case 24, the overall cost of the lighting system is minimized.

Figure 10:
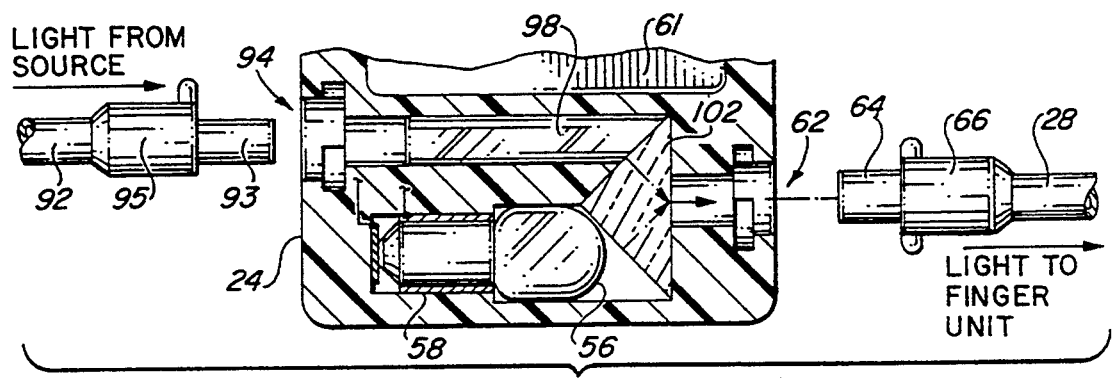
FIG. 10 is a partial sectional view of an alternate embodiment of the wrist-supported component of the illumination system, including a light transmitting prism for alternately transmitting light received from either a local light bulb or a remote light source into the light output port of the illumination system.

FIG. 10 is a schematic drawing showing the components housed within case 24. Components which have been described above, including light bulb 56, battery 61, and slide switch 65, are designated by like reference numerals in FIG. 10. Recharging plug 80 is shown inserted within electrical jack 67 for recharging battery 61. A voltage dropping resistor 82 is connected in series with electrical jack 67 and battery 61. In the preferred embodiment of the present invention, rechargeable batteries 61 are of the type commercially available from Sanyo under Model No. KFA900 and provide a voltage source of 3 volts when fully-charged. Light bulb 56 is preferably of the type commercially available from Mini-Mag-Lite and is designed to operate at 3 volts. The external charging circuit provides a nominal output voltage of 3 volts to recharge batteries.

Figure 11:
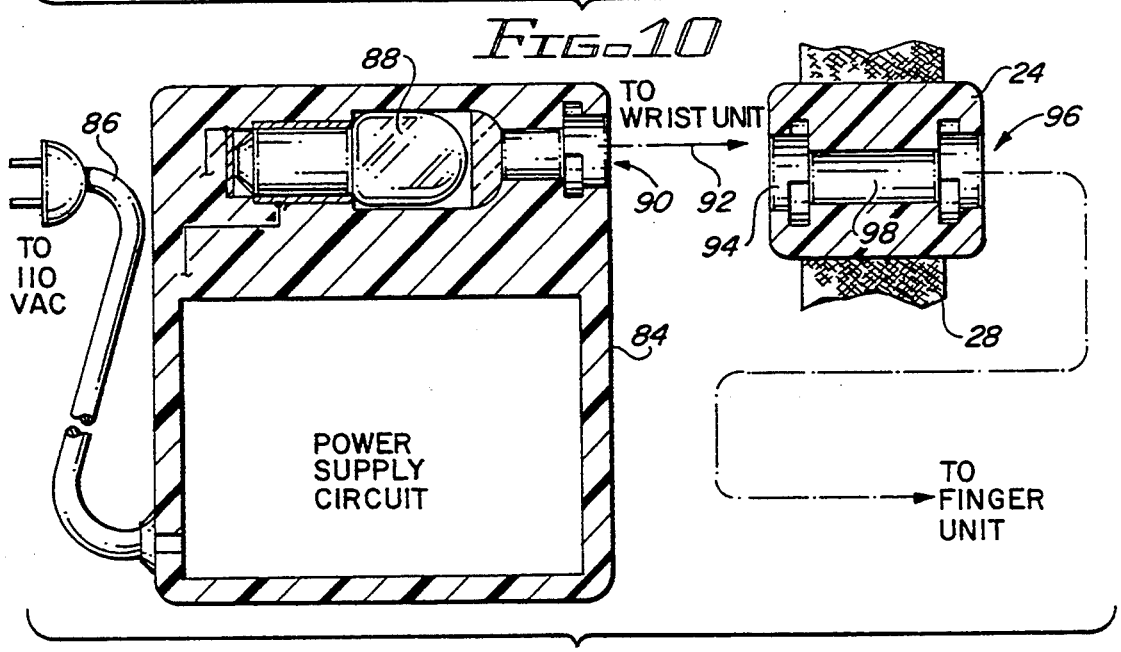
FIG. 11 is a sectional schematic view of a remote light source used to supply light to a light tunnel within the wrist-supported case of the illumination system.

As noted above, some dentists, oral surgeons, and other physicians may already have available within their facilities sources of light adapted to illuminate fiber optic cables. For example, it has already been noted that some dentists have in the past used dental handpieces that include a fiber optic light path. Accordingly, an alternate embodiment of the present invention is shown in FIGS. 5, 7, and 11, wherein the source of the light conducted by fiber optic light conductor 28 to the field of operation can be located remotely from case 24, rather than being generated locally within case 24. As shown in FIG. 11, a remote light source 84 includes a power supply cord 86 for being plugged into an electrical receptacle. Remote light source houses a power supply circuit for driving a light bulb 88 and thereby providing a source of light. Remote light source 84 includes a light output port 90 disposed proximate light bulb 88 and adapted to receive an end of a fiber optic light conductor 92 (see FIG. 7). As shown in FIG. 11, light output port 90 may be of the same quick-release bayonet-style construction as described above in conjunction with light outport port 62 (see FIG. 5). Likewise, the end of fiber optic light conductor 92 that is received within light output port 90 of remote light source 84 may be provided with a connector similar to connector 66.

Still referring to FIG. 11, wrist-supported case 24 is shown having a light input port 94, a light output port 96, and a connecting light tunnel 98. Light input port 94 may be of the same quick-release bayonet-style construction as described above in conjunction with light outport port 62 (see FIG. 5). Likewise, the opposing second end 93 of fiber optic light conductor 92 (see FIG. 5) that is received within light input port 94 of wrist-supported case 24 may be provided with a connector 95 similar to connector 66. Accordingly, second end 93 of fiber optic light conductor 92 may be easily detached from wrist-supported case 24 when lighting device 20 is not in use. Light output port 96 preferably has the same construction as described above with respect to light output port 62 for being releasably coupled to first end 64 of fiber optic light conductor 28.

In operation, fiber optic light conductor 92 has its first end inserted into light output port 90 of remote light source 84 for causing light provided by light bulb 88 to be conducted through fiber optic light conductor 92 and emitted by the opposing second end 93 thereof into light tunnel 98. First end 64 of fiber optic light conductor 28 is inserted into light output port 96 (see FIG. 5), thereby allowing light emitted by end 93 of light conductor 92 to be transferred into first end 64 of light conductor 28 for transmission to the second end of light conductor 28 in order to shine a beam of light through lens 44. Preferably, light tunnel 98 has walls coated with reflective material 100 (see FIG. 7) to reduce light losses that might otherwise result due to absorption by the walls of light tunnel 98.

FIGS. 5 and 7 illustrate a lighting device adapted to be used with either a remote light source or an internally generated light source. Within FIGS. 5 and 7, those components needed for internal generation of the light source, as previously described in conjunction with FIGS. 1–3 and 9, are referenced by like reference numerals, while those components used to convey light from a remote light source through a light tunnel in case 24 to fiber optic light conductor 28, as described in conjunction with FIG. 11, are identified by like reference numerals. As shown in FIG. 5, first end 64 of light conductor 28 may be coupled to either output light port 62 (for internal generation of the light source) or output light port 96 (when using remote light source 84).

FIG. 10 shows yet another embodiment of the lighting device generally shown in FIG. 5. In the alternate embodiment of FIG. 11, a prism 102 directs light from either light bulb 56 or light tunnel 98 into light output port 62. Consequently, second output light port 96 is omitted, and first end 64 of light conductor 28 is inserted into a single light output port irrespective of whether light bulb 56 is providing the source of light or a remote light source is providing the source of light.

Figure 12:
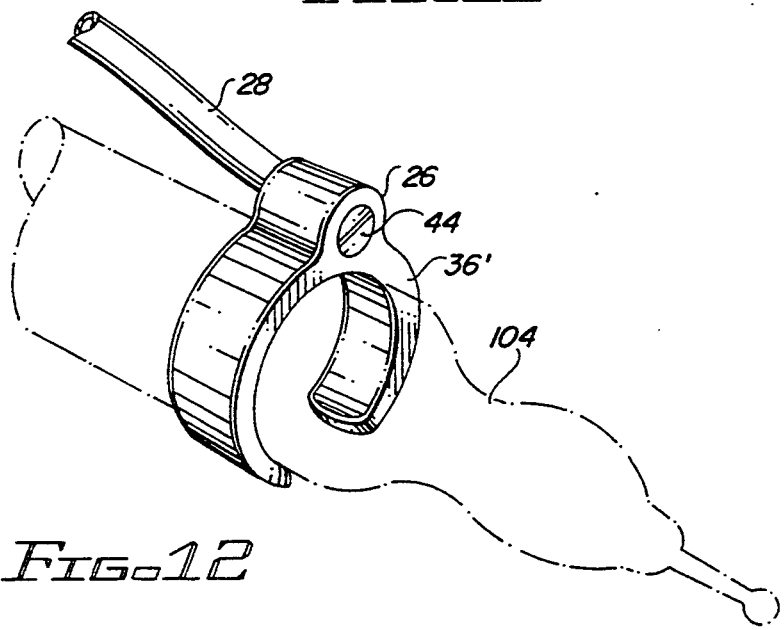
FIG. 12 is a partial perspective view of the finger-mounted component of the illumination system shown in the form of a ring for releasably engaging the housing of a dental handpiece shown in dashed outline.

Finally, FIG. 10 shows an alternate form of finger-supported component 26 wherein a split ring 36' is provided instead of a strap. As shown in FIG. 12, split ring 36' may, if desired, be secured about a dental handpiece, shown in dashed outline by reference numeral 104, rather than being worn about a finger in order to illuminate the area of the field of operation at which the dental handpiece is directed.

Those skilled in the art will now appreciate that a fiber optic illumination system has now been described which allows a dentist, oral surgeon, or other physician to conveniently position a light beam into the oral cavity or other field of operation without obstructing other tools to be inserted into the field of operation. The described lighting device can be supported independently of other tools, and the amount of light provided by such lighting device is not restricted by any requirement for passage of fiber optic light conductors through dental tools. The described lighting device allows the user to economically sterilize portions that come in contact with the field of operation while minimizing delays during sterilization and minimizing the costs of replicating the entire lighting device. In addition, the described lighting device may be provided in a form which provides its own source of light or which can be used in conjunction with existing remote light sources.

While the present invention has been described with respect to certain preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

I claim:

1. A dental lighting device for allowing a dentist to selectively illuminate a portion of a patient's mouth, said lighting device comprising in combination:
   a. a case;
   b. case support means for releasably supporting said case upon a dentist's arm;
   c. a light source supported by said case for providing light;
   d. a fiber optic light conductor having first and second opposing ends;
   e. coupling means for detachably coupling the first end of said fiber optic light conductor to said case for causing light provided by said light source to enter the first end of said fiber optic light conductor for being conducted through said fiber optic light conductor toward the second end thereof for being emitted therefrom;
   f. finger support means for supporting the second end of said fiber optic light conductor upon a finger of the dentist for directing light conducted by said fiber optic light conductor and emitted from the second end thereof into the patient's mouth;
   g. said coupling means allowing said fiber optic light conductor and said finger support means to be detached from said case for allowing said fiber optic light conductor and finger support means to be sterilized in a sterilization apparatus between uses, while avoiding any need to insert said case, case support means, and light source within the sterilization apparatus;

said dental lighting device further including:
   h. a second fiber optic light conductor having first and second opposing ends, said second fiber optic light conductor being essentially identical to the first fiber optic light conductor; and
   i. second finger support means essentially identical to the first finger support means for supporting the second end of said second fiber optic light conductor upon a finger of the dentist for directing light emitted from the second end of said second fiber optic light conductor into the patient's mouth; whereby said second fiber optic light conductor and second finger support means can be detachably coupled by said coupling means to said case for causing light provided by said light source to be emitted from the second end of said second fiber optic light conductor during sterilization of the first fiber optic light conductor and first finger support means.

* * * * *